United States Patent [19]

Tsutsumi et al.

[11] 4,132,679

[45] Jan. 2, 1979

[54] LOW IRRITANT SHAMPOO COMPOSITION

[75] Inventors: Hisao Tsutsumi, Sakura; Hiroshi Watanabe, Funabashi; Shizuo Hayashi, Saitama, all of Japan

[73] Assignee: Kao Soap Co., Ltd., Tokyo, Japan

[21] Appl. No.: 821,911

[22] Filed: Aug. 4, 1977

[30] Foreign Application Priority Data

Aug. 24, 1976 [JP] Japan ................................ 51-101005

[51] Int. Cl.$^2$ ......................... C11D 1/38; C11D 3/26; C11D 7/32
[52] U.S. Cl. .................................. 252/545; 252/89 R; 252/DIG. 13; 252/DIG. 14; 252/546; 252/547; 424/70
[58] Field of Search ................. 252/545, 546, 547, 89, 252/DIG. 13, DIG. 14; 424/70

[56] References Cited

U.S. PATENT DOCUMENTS

| 3,755,559 | 8/1973 | Hewitt | 252/545 X |
| 3,778,379 | 12/1973 | Papannou | 252/545 X |

FOREIGN PATENT DOCUMENTS

| 240153 | 3/1969 | U.S.S.R. | 252/545 |
| 1049732 | 8/1963 | United Kingdom | 252/545 |

*Primary Examiner*—Mayer Weinblatt
*Attorney, Agent, or Firm*—Blanchard, Flynn, Thiel, Boutell & Tanis

[57] ABSTRACT

A liquid shampoo composition comprising an aqueous solution of (A) monoalkyl ester salt of phosphoric acid and (B) trialkylaminoacetobetaine, trialkylaminopropanesulfobetaine or mixture thereof. The composition possesses high detergency, high foaming and low skin irritation properties.

10 Claims, No Drawings

LOW IRRITANT SHAMPOO COMPOSITION

BACKGROUND OF THE INVENTION

1. Field of the Invention

The present invention relates to a shampoo composition which does not cause skin irritation and roughness. The composition comprises a monoalkyl ester salt of phosphoric acid as an active detergent component and a trialkylaminoacetobetaine or trialkylaminopropane-sulfobetaine blended with the active detergent component at a specific ratio.

2. DESCRIPTION OF THE PRIOR ART

As surface active agents for shampoos, there have heretofore been widely used anionic surface active agents such as alkyl ester salts of sulfuric acid, polyoxyethylene alkyl ester salts of sulfuric acid, alkylbenzenesulfonic acid salts and α-olefinsulfonic acid salts. However, it has been confirmed that these surface active agents cause skin irritation to a greater or lesser degree, and when shampoos containing these surface active agents are used repeatedly, roughening of the skin readily occurs. It is known that non-ionic surface active agents cause little or no skin irritation, but they are inferior to anionic surface active agents in foaming power and detergency. Therefore, incorporation of non-ionic surface active agents into detergents, such as shampoos, is not preferred. Surface active agents of the phosphoric acid ester type are known as anionic surface active agents in the art, but since each of the conventional surface active agents of the phosphoric acid ester type is a mixture of a monoester and a diester or a mixture of a monoester, a diester and a triester, if they are used in their normal state, their water solubility is extremely low and they do not manifest a substantial foaming power. Therefore, the use of these surface active agents in detergent compositions involves various difficulties.

SUMMARY OF THE INVENTION

We have discovered a shampoo composition which does not irritate or roughen the skin, which has a good foaming power and which imparts a good feel or touch to hair after shampooing. According to our invention, there is provided a shampoo composition comprising as the main surfactant component, from 1 to 40% by weight of one or a mixture of two or more monoalkyl ester salt of phosphoric acid having the formula (1):

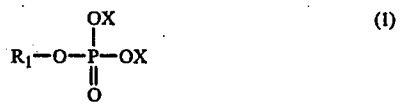   (1)

wherein $R_1$ is straight-chain alkyl having an average carbon atom number of from 10 to 14, a straight-chain unsaturated hydrocarbon group, preferably alkenyl, having an average carbon atom number of from 10 to 18, a branched-chain alkyl having an average carbon atoms number of from 10 to 18 or a branched-chain unsaturated hydrocarbon group, preferably alkenyl, having an average carbon atom of from 10 to 18, and X is selected from hydrogen, alkali metal, ammonium, lower alkyl ammonium and hydroxyalkyl ammonium, with the proviso that both X's are not hydrogen simultaneously. It also was found that when from 0.1 to 40% by weight of one or a mixture of two or more members selected from the group consisting of trialkylaminoacetobetaines having the formula (2):

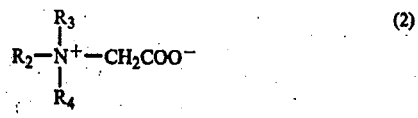   (2)

wherein $R_2$ is a hydrocarbon group, preferably alkyl, having an average carbon atom number of from 10 to 16 and $R_3$ and $R_4$ each is lower alkyl having from 1 to 3 carbon atoms, and trialkylaminopropane-sulfobetaines having the formula (3):

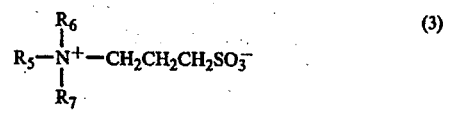   (3)

wherein $R_5$ is alkyl having an average carbon atom number of from 10 to 16 and $R_6$ and $R_7$ each is alkyl having from 1 to 3 carbon atoms, is contained in the shampoo composition, the properties of detergency, foaming power and water solubility are greatly improved in comparison with compositions containing lauryl diethanolamide, which has heretofore been used as a foam stabilizer or foaming agent for conventional surface active agents such as sodium alkylbenzenesulfonates and the like. Also, the skin-irritating activity is maintained at a very low level in the shampoo composition according to this invention.

The monoalkyl ester salt of phosphoric acid of the formula (1) is obtained, for example, by hydrolyzing a mono-long-chain-alkyl phosphorodichloridate formed by reacting phosphorus oxychloride with a long-chain aliphatic alcohol. When a long-chain aliphatic alcohol is phosphated, a dialkyl ester salt of phosphoric acid is formed as a by-product in addition to the desired monoalkyl ester salt of phosphoric acid under some reaction conditions. The monoalkyl ester salt of phosphoric acid referred to in the present invention may contain up to 25% by weight, based on the monoalkyl ester salt of phosphoric acid, of such dialkyl ester salt of phosphoric acid formed as a by-product.

The straight-chain alkyl having an average carbon atom number of from 10 to 14, which is referred to in the present invention for "$R_1$" in formula (1), includes decyl, undecyl, dodecyl, tridecyl and tetradecyl groups and mixtures thereof. Further, it may further comprise straight-chain alkyl groups having an average carbon atom number outside the range of 10 to 14, provided that the average carbon atom number for "$R_1$" in formula (1) as a whole is in the range of from 10 to 14. The straight-chain unsaturated hydrocarbon group having an average carbon atom number of from 10 to 18, for "$R_1$" in formula (1) includes, for example, ethylenically unsaturated hydrocarbon groups, preferably alkenyl groups, corresponding to decyl, undecyl, dodecyl, tridecyl, tetradecyl, pentadecyl, hexadecyl, heptadecyl and octadecyl groups, and such groups having an average carbon atom number of from 16 to 18 are preferred. Further, mixtures of these groups can be used, and the group may further comprise a straight-chain unsaturated hydrocarbon group, such as alkenyl, having an average carbon atom number outside the range of from 10 to 18, provided that the average carbon atom number as a whole, is in the range of from 10 to 18. The branched-chain saturated or unsaturated hydrocarbon group, such as alkyl or alkenyl, having an average carbon atom number of from 10 to 18 for "$R_1$" of formula (1), includes branched acyclic alkyl or alkenyl groups and cycloalkyl and cycloalkenyl groups. These groups may be either saturated or ethylenically unsaturated, and mixtures of them can be used. For example, there can be mentioned branched decyl, branched dodecyl, branched tridecyl, branched tetradecyl, branched pentadecyl, branched hexadecyl, branched heptadecyl and branched octadecyl groups. These groups may further comprise branched alkyl groups having an average carbon atom number outside the range of from 10 to 18, provided that the average carbon atom number as a whole is in the range of 10 to 18. Such groups having an average carbon atom number of from 16 to 18 are especially preferred.

The alkali metal referred to for "X" for formula (1) in the present invention includes lithium, potassium and sodium. Sodium and potassium are preferred.

The lower alkyl ammonium ion or hydroxyalkyl ammonium ion referred to for "X" for formula (1) in the present invention is a cation formed by quaternizing a corresponding amine used for neutralizing phosphoric acid in the process for the preparation of the monoalkyl ester salt of phosphoric acid of the formula (1), after the neutralization step. The corresponding amine includes primary, secondary and tertiary amines having an alkyl or hydroxy group-containing alkyl group having 1 to 3 carbon atoms. For example, there can be mentioned dimethylmonoethanolamine, methyldiethanolamine, trimethylamine, triethylamine, dibutylamine, butyldimethylamine, monoethanolamine, diethanolamine, triethanolamine, isopropyldimethylamine and isopropylethanolamine. Monoethanolamine, diethanolamine and triethanolamine are preferred, and triethanolamine (TEA) is especially preferred.

The shampoo composition of the present invention comprises from 1 to 40% by weight of the compound of the above formula (1) and from 0.1 to 40% by weight of the compound of the above formula (2) and/or the compound of the above formula (3). The mixing weight ratio of the compound of the formula (1) to the compound of the formula (2) or (3) is preferably from 95/5 to 45/55, and the mixing weight ratio of the compound of the formula (1) to a mixture of the compounds of the formulae (2) and (3) is preferably from 95/5 to 55/45.

In addition to (A) the compound of the formula (1), (B) the compound of the formula (2) and/or the compound of the formula (3) and (C) water, the shampoo composition of the present invention may comprise customary adjunct components conventionally used in shampoos, for example, solubilizing agents such as propylene glycol, glycerin and urea, viscosity adjusting agents such as ethanol, inorganic salts (for example, NaCl and $NH_4Cl$) and higher alcohols, perfumes, dyes, ultraviolet absorbers, antioxidants, dandruff-removing agents, fungicides and antseptics.

The present invention will now be further described by reference to the following illustrative Examples.

EXAMPLE 1

The foaming test and the water solubility test were conducted by using mixtures containing the compounds of the present invention and having the compositions indicated below. In the foaming test, 0.1 wt.% of lanolin was added as an artificial soil to a 0.5% aqueous solution of the composition and the mixture was stirred in a cylindrical vessel for 5 minutes at 25° C. using a flat propeller rotated at 1000 rpm. The rotation direction was reversed at intervals of 10 seconds. After 30 seconds had passed from completion of the stirring, the foaming property was evaluated based on the volume of foam remaining on top of the solution. The water solubility was evaluated based on the appearance of a 1% aqueous solution of the composition at 20° C. Lauryl diethanolamide which is widely regarded as being an effective foam stabilizer or foaming agent for conventional anionic surface active agents was used as a comparative ingredient.

The results obtained are shown in Table 1. The weight ratio of the compound of the formula (1) to the compound of the formula (2) and/or the compound of the formula (3) used in the various tests are as follows.

| Sample No. | Weight Ratio of Compound (1):Compound (2) | Sample No. | Weight Ratio of Compound (1):Compound (3) | Sample No. | Weight Ratio of Compound (1):Compound (2):Compound (3) | Sample No. | Weight Ratio of Compound (1):Lauryl Diethanolamide (comparison) |
|---|---|---|---|---|---|---|---|
| 1 (comparison) | 100:0 | 7 | 90:10 | 12 | ?: 5: 5 | 18 (comparison) | 90:10 |
| 2 | 90:10 | 8 | 80:20 | 13 | 80:10:10 | 19 (comparison) | 80:20 |
| 3 | 80:20 | 9 | 50:50 | 14 | 60:20:20 | 20 (comparison) | 50:50 |
| 4 | 50:50 | 10 | 30:70 | 15 | 60:30:10 | 21 (comparison) | 30:70 |
| 5 | 30:70 | 11 (comparison) | 0:100 | 16 | 50:25:25 | 22 (comparison) | 0:100 |
| 6 (comparison) | 0:100 | | | 17 (comparison) | 0:50:50 | | |

Table 1

| Foaming and Water-Solubility Test Results | | |
|---|---|---|
| $R_1$ in Compound (1) | $C_{10}H_{21}$ | $C_{12}H_{25}$ |
| X in Compound (1) | H, K | H, Na |
| $R_2$ in Compound (2) | $C_{12}H_{25}$ | $C_{12}H_{25}$ |

Table 1-continued
Foaming and Water-Solubility Test Results

| | | | | | |
|---|---|---|---|---|---|
| ($R_3$, $R_4$ = methyl) $R_5$ in Compound (3) ($R_6$, $R_7$ = methyl) | | $C_{12}H_{25}$ | | $C_{12}H_{25}$ | |
| Components Used | Mixing Ratio (Sample No.) | Volume of foam (ml) | Water Solubility | Volume of foam (ml) | Water Solubility |
| (1) | 1 (comparison) | 185 | transparent | 204 | turbid |
| | 2 | 235 | transparent | 258 | transparent |
| (1) and (2) | 3 | 281 | " | 321 | " |
| | 4 | 221 | | 228 | |
| | 5 | 216 | " | 218 | |
| (2) | 6 (comparison) | 210 | transparent | 210 | transparent |
| | 7 | 258 | transparent | 302 | transparent |
| (1) and (3) | 8 | 298 | " | 342 | " |
| | 9 | 218 | " | 265 | " |
| | 10 | 200 | " | 201 | " |
| (3) | 11 (comparison) | 186 | transparent | 186 | transparent |
| | 12 | 241 | transparent | 280 | transparent |
| (1), (2) and (3) | 13 | 293 | " | 328 | " |
| | 14 | 216 | " | 245 | " |
| | 15 | 218 | " | 252 | " |
| | 16 | 204 | " | 210 | " |
| (2) and (3) | 17 (comparison) | 194 | transparent | 194 | transparent |
| | 18 (comparison) | 192 | transparent | 200 | transparent |
| (1) and dilauryl diethanol-amide | 19 (comparison) | 185 | " | 180 | " |
| | 20 (comparison) | 173 | " | 154 | " |
| | 21 (comparison) | 118 | " | 125 | " |
| lauryl diethanol-amide | 22 (comparison) | 108 | transparent | 108 | transparent |

| | | | |
|---|---|---|---|
| $R_1$ in Compound (1) | | $C_{14}H_{29}$ | $C_{14}H_{29}$ |
| X in Compound (1) | | Na, Na | H, TEA |
| $R_2$ in Compound (2) | | $C_{14}H_{29}$ | $C_{14}H_{29}$ |
| ($R_3$, $R_4$ = methyl) $R_5$ in Compound (3) ($R_6$, $R_7$ = methyl) | | $C_{14}H_{29}$ | $C_{14}H_{29}$ |

| Components Used | Mixing Ratio (Sample No.) | Volume of foam (ml) | Water Solubility | Volume of foam (ml) | Water Solubility |
|---|---|---|---|---|---|
| (1) | 1 (comparison) | 210 | slightly turbid | 242 | transparent |
| | 2 | 240 | transparent | 298 | transparent |
| (1) and (2) | 3 | 256 | " | 346 | " |
| | 4 | 214 | " | 285 | " |
| | 5 | 206 | " | 212 | " |
| (2) | 6 (comparison) | 203 | slightly turbid | 203 | slightly turbid |
| | 7 | 245 | transparent | 264 | transparent |
| (1) and (3) | 8 | 287 | " | 298 | " |
| | 9 | 216 | " | 228 | " |
| | 10 | 202 | " | 201 | " |
| (3) | 11 (comparison) | 190 | slightly turbid | 190 | slightly turbid |
| | 12 | 248 | transparent | 285 | transparent |
| | 13 | 262 | " | 304 | " |
| (1), (2) and (3) | 14 | 241 | " | 267 | " |
| | 15 | 212 | " | 235 | " |
| | 16 | 203 | " | 212 | " |
| (2) and (3) | 17 (comparison) | 196 | slightly turbid | 196 | slightly turbid |
| | 18 (comparison) | 212 | slightly turbid | 240 | transparent |
| (1) and dilauryl diethanol-amide | 19 (comparison) | 200 | " | 198 | " |
| | 20 (comparison) | 195 | " | 154 | " |
| | 21 (comparison) | 135 | " | 116 | " |
| lauryl diethanol-amide | 22 (comparison) | 108 | transparent | 108 | transparent |

| | | | |
|---|---|---|---|
| $R_1$ in Compound (1) | | $C_{16}H_{33}$ (comparison) | $C_{18}H_{35}$ |
| X in Compound (1) | | H, K | K, K |
| $R_2$ in Compound (2) | | $C_{12}H_{25}$ | $C_{12}H_{25}$ |
| ($R_3$, $R_4$ = methyl) $R_5$ in Compound (3) ($R_6$, $R_7$ = methyl) | | $C_{12}H_{25}$ | $C_{12}H_{25}$ |

| Components Used | Mixing Ratio (Sample No.) | Volume of foam (ml) | Water Solubility | Volume of foam (ml) | Water Solubility |
|---|---|---|---|---|---|
| (1) | 1 (comparison) | 63 | turbid | 201 | transparent |
| | 2 | 68 | turbid | 235 | transparent |
| (1) and (2) | 3 | 69 | " | 262 | " |
| | 4 | 85 | " | 215 | " |
| | 5 | 120 | slightly turbid | 212 | " |

Table 1-continued
Foaming and Water-Solubility Test Results

| | | | | | |
|---|---|---|---|---|---|
| (2) | 6 (comparison) | 210 | transparent | 210 | transparent |
| | 7 | 63 | turbid | 228 | transparent |
| (1) | 8 | 75 | " | 245 | " |
| and | 9 | 84 | " | 218 | " |
| | 10 | 118 | " | 203 | " |
| (3) | 11 (comparison) | 186 | transparent | 186 | transparent |
| | 12 | 68 | turbid | 216 | transparent |
| (1), (2) | 13 | 69 | " | 254 | " |
| and | 14 | 72 | " | 232 | " |
| (3) | 15 | 70 | " | 240 | " |
| (2) and (3) | 17 (comparison) | 194 | transparent | 194 | transparent |
| | 18 (comparison) | 58 | turbid | 200 | transparent |
| (1) and | 19 (comparison) | 45 | " | 200 | " |
| dilauryl diethanolamide | 20 (comparison) | 72 | " | 198 | " |
| lauryl | 21 (comparison) | 68 | " | 116 | " |
| diethanolamide | 22 (comparison) | 108 | transparent | 108 | transparent |

As will be apparent from the results shown in Table 1, when the compound (1) is mixed with the compound (2) or (3), the foaming property is greatly improved in comparison with compositions wherein the compound (1) alone is used, and also the water solubility is improved. In contrast, lauryl diethanolamide, which is known to have a foam increasing effect for conventional anionic surface active agents, does not exhibit such synergistic effects with the compound (1).

It is believed that the above synergistic effects attained by the combination of compound (1) and the compound (2) and/or (3) is owing to a reduction of the Krafft point. Accordingly, if the average carbon atom number is larger than 14 when "$R_1$" is straight-chain alkyl in the compound (1), the Krafft point becomes too high and the compound (1) is poorly soluble in water at room temperature, and no substantial synergistic effect with the compound (2) and/or (3) is attained. In contrast, even if the carbon chain length is 18, when the compound (1) includes ethylenically unsaturated linkages, the Krafft point is lowered and a synergistic effect with the compound (2) and/or (3) is attained.

Accordingly, a suitable average carbon atom number in the compound (1) is from 10 to 14 when $R_1$ is straight-chain alkyl, whereas it is from 10 to 18 when $R_1$ is unsaturated or branched hydrocarbon.

The best results are obtained when the mixing weight ratio of the compound (1) to the compound (2) and/or (3) is in the range of from 90/10 to 70/30, especially about 80/20, but even if the mixing weight ratio is outside this optimum range, the intended effects can be attained.

EXAMPLE 2

Typical examples of the compositions shown in Example 1 and comparative surface active agents customarily used for shampoos were subjected to a closed patch skin irritation test. Each sample was used in the form of a 2% aqueous solution. Three groups of guinea pigs, each consisting of 6 guinea pigs, were used for each sample. Patches were applied for 24 hours, and when 24 hours had passed after removal of the patches, the degree of the skin irritation was evaluated based on the intensities of the skin reactions, namely redness ($\pm$ to ++), edema ($\pm$ to ++) and negative (no irritation), by seven degrees. A score of 0.5 was given to $\pm$, 1.0 point was given to + and 2.0 points were given to ++. A score of zero was given when no skin irritation occurred. In short, the skin-irritating property was evaluated based on the total score of the redness and edema. The results obtained are shown in Table 2.

Table 2
Degree of Skin Irritation

| Sample* | Mixing Weight Ratio | | | Score of 24 Hours' Close Patch Test | Other Change on Skin |
|---|---|---|---|---|---|
| | Compound (1) | Compound (2) | Compound (3) | | |
| Present Invention | | | | | |
| a | 80 | 20 | 0 | 0.5 | same as in case of water |
| b | 30 | 70 | 0 | 1.5 | " |
| c | 80 | 0 | 20 | 0 | " |
| d | 30 | 0 | 70 | 0.5 | " |
| e | 60 | 20 | 20 | 1.0 | " |
| Comparison (1) | | | | | |
| f | 100 | 0 | 0 | 0 | " |
| g | 0 | 100 | 0 | 4.5 | slightly lustrous |
| h | 0 | 0 | 100 | 2.0 | same as in case of water |
| Comparison (2) | | | | | |
| sodium laurylsulfate | | | | 28.0 | extreme scaling |
| sodium dodecylbenzenesulfonate | | | | 18.0 | medium scaling |
| sodium α-olefinsulfonate | | | | 6.0 | slight scaling |
| sodium α-dodecenesulfonate | | | | 16.0 | extreme scaling |
| sodium dodecylpolyoxyethylenesulfate | | | | 8.0 | slightly lustrous |
| water | | | | 0 | not changed |

| Sample | Compound (1) | | Compound (2) | | Compound (3) | |
|---|---|---|---|---|---|---|
| | $R_1$ | X | $R_2$ | $R_3$, $R_4$ | $R_5$ | $R_6$, $R_7$ |
| a | $C_{12}H_{25}$ | H,Na | $C_{12}H_{25}$ | $CH_3$ | — | — |
| b | $C_{12}H_{25}$ | H,Na | $C_{12}H_{25}$ | $CH_3$ | — | — |
| c | $C_{14}H_{29}$ | H,TEA | — | — | $C_{12}H_{25}$ | $CH_3$ |
| d | $C_{14}H_{29}$ | H,TEA | — | — | $C_{12}H_{25}$ | $CH_3$ |
| e | $C_{12}H_{25}$ | H,Na | $C_{12}H_{25}$ | $CH_3$ | $C_{12}H_{25}$ | $CH_3$ |
| f | $C_{12}H_{25}$ | H,Na | — | — | — | — |

-continued

| Sample | Compound (1) | | Compound (2) | | Compound (3) | |
|---|---|---|---|---|---|---|
| | $R_1$ | X | $R_2$ | $R_3, R_4$ | $R_5$ | $R_6, R_7$ |
| g | — | — | $C_{12}H_{25}$ | $CH_3$ | — | — |
| h | — | — | — | — | $C_{12}H_{25}$ | $CH_3$ |

As will be apparent from the result shown in Table 2, the composition of the present invention exhibits no substantial skin irritation property, whereas conventional shampoo bases have a considerable skin irritation property.

EXAMPLE 3

Shampoos (A) to (C) of the present invention having the compositions indicated below were prepared and subjected to a hair-washing test in order to examine the foaming property and the feel or touch of the hair after shampooing. For comparison, shampoos comprising a conventional shampoo base were similarly tested.

| Samples of Present Invention | |
|---|---|
| Shampoo A: | |
| Monosodium monolaurylphosphate | 15% |
| Lauryldimethylaminoacetobetaine | 5% |
| Glycerin | 3% |
| Perfume | 0.3% |
| Water | balance |
| Shampoo B: | |
| Monotriethanolamine monomyristylphosphate | 12% |
| Monotriethanolamine dimyristylphosphate | 3% |
| Lauryldimethylaminopropane-sulfobetaine | 7% |
| Propylene glycol | 5% |
| Perfume | 0.3% |
| Water | balance |
| Shampoo C: | |
| Monotriethanolamine monolaurylphosphate | 12% |
| Triethanolamine dilaurylphosphate | 3% |
| Lauryldimethylaminoacetobetaine | 3% |
| Lauryldimethylaminopropane-sulfobetaine | 3% |
| Glycerin | 2% |
| Perfume | 0.5% |
| Water | balance |
| Comparative Samples | |
| Shampoo (D): | |
| Sodium laurylsulfate | 15% |
| Glycerin | 5% |
| Perfume | 0.3% |
| Water | balance |
| Shampoo (E): | |
| Sodium polyoxyethylene laurylsulfate | 13% |
| Lauryldimethylaminoacetobetaine | 3% |
| Glycerin | 2% |
| Perfume | 0.3% |
| Water | balance |
| Shampoo (F): | |
| Triethanolamine laurylsulfate | 12% |
| Lauryl diethanolamide | 3% |
| Propylene glycol | 2% |
| Perfume | 0.3% |
| Water | balance |

As a result, it was found that samples (A) to (C) are superior or comparable to samples (D) to (F) with respect to the foaming property, and with respect to the feel of foams, samples (A) to (C) of the present invention are much superior to comparative samples (D) to (F) and the hairs washed with the samples of the present invention are soft and manageable and are easily combed.

As will be apparent from the results of Examples 1 to 3, when it is desired to obtain shampoos having a good foaming property and no skin irritation property, if conventional known surface active agents are employed, it is difficult to satisfy both requirements simultaneously, but when the composition of the present invention is used, it is possible to obtain a shampoo having no skin irritation property without reduction of the detergency required of a shampoo.

The embodiments of the invention in which an exclusive property or privilege is claimed are defined as follows:

1. A shampoo composition consisting essentially of (A) from one to 40% by weight of one or a mixture of two or more monoalkyl ester salts of phosphoric acid having the formula (1):

$$R_1O-\overset{\overset{\displaystyle O}{\|}}{\underset{\underset{\displaystyle OX}{|}}{P}}-OX \qquad (1)$$

wherein $R_1$ is straight-chain alkyl having an average carbon atom number of from 10 to 14, straight-chain alkenyl having an average carbon atom number of from 10 to 18, branched-chain or alicyclic alkyl having an average carbon atom number of from 10 to 18, or branched-chain or alicyclic alkenyl having an average carbon atom number of from 10 to 18, and X is selected from the group consisting of hydrogen, alkali metal, ammonium, lower alkyl ($C_1$ to $C_3$) ammonium and hydroxyalkyl ($C_1$ to $C_3$) ammonium, with the proviso that both X's are not hydrogen simultaneously, (B) from 0.1 to 40% by weight of one member or a mixture of two or more members selected from the group consisting of trialkylaminoacetobetaines having the formula (2):

$$R_2-\overset{\overset{\displaystyle R_3}{|}}{\underset{\underset{\displaystyle R_4}{|}}{N^+}}-CH_2COO^- \qquad (2)$$

wherein $R_2$ is alkyl or alkenyl having an average carbon atom number of from 10 to 16 and $R_3$ and $R_4$ each is alkyl having from one to 3 carbon atoms, and trialkylaminopropane-sulfobetaines having the formula (3):

$$R_5-\overset{\overset{\displaystyle R_6}{|}}{\underset{\underset{\displaystyle R_7}{|}}{N^+}}-CH_2CH_2CH_2SO_3^- \qquad (3)$$

wherein $R_5$ is alkyl having an average carbon atom number of from 10 to 16 and $R_6$ and $R_7$ each is alkyl having from one to 3 carbon atoms,
and (C) the balance is essentially water.

2. A shampoo composition as set forth in claim 1 wherein component B consists of compound or compounds of the formula (2), and wherein the mixing weight ratio of A/B is in the range of 95/5 to 45/55.

3. A shampoo composition as set forth in claim 1 wherein component B consists of compound or compounds of the formula (3), and wherein the mixing weight ratio of A/B is in the range of 95/5 to 45/55.

4. A shampoo composition as set forth in claim 1 which contains a mixture of formula (2) and formula (3) compounds, and wherein the weight ratio of A/B is in the range of from 95/5 to 55/45.

5. A shampoo composition as set forth in claim 1 wherein $R_1$ is straight-chain alkyl having an average carbon atom number of from 10 to 14, straight-chain alkenyl having an average carbon atom number of from 16 to 18 or a branched alkyl or alkenyl having an average carbon atom number of from 16 to 18, $R_2$ is straight-chain alkyl having an average carbon atom number of 10 to 16, and $R_5$ is straight-chain alkyl having an average carbon atom number of from 10 to 16.

6. A shampoo composition as set forth in claim 1 wherein the alkali metal is sodium, potassium or lithium and the hydroxyalkyl ammonium is a quaternized ion of monoethanolamine, diethanolamine or triethanolamine.

7. A shampoo composition as set forth in claim 1 wherein each of $R_3$, $R_4$, $R_6$ and $R_7$ is methyl.

8. A shampoo composition as set forth in claim 1 which comprises a monolauryl ester salt of phosphoric acid having the formula

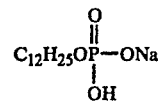

and lauryldimethylaminopropane-sulfobetaine having the formula:

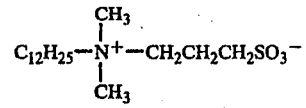

at a weight of A/B of 80/20.

9. A shampoo composition according to claim 1 in which the mixing weight ratio of A/B is in the range of from 90/10 to 70/30.

10. A shampoo composition according to claim 1 in which the mixing weight ratio of A/B is in the range of about 80/20.

* * * * *